(12) United States Patent
Nazzaro

(10) Patent No.: US 10,751,478 B2
(45) Date of Patent: Aug. 25, 2020

(54) MULTI-STAGE DELIVERY SYSTEM

(71) Applicant: Insulet Corporation, Acton, MA (US)

(72) Inventor: David Nazzaro, Groveland, MA (US)

(73) Assignee: INSULET CORPORATION, Acton, MA (US)

(*) Notice: Subject to any disclaimer, the term of this patent is extended or adjusted under 35 U.S.C. 154(b) by 352 days.

(21) Appl. No.: 15/724,541

(22) Filed: Oct. 4, 2017

(65) Prior Publication Data

US 2018/0099100 A1 Apr. 12, 2018

Related U.S. Application Data

(60) Provisional application No. 62/405,489, filed on Oct. 7, 2016.

(51) Int. Cl.

| | | |
|---|---|---|
| *A61M 5/315* | (2006.01) | |
| *A61M 5/28* | (2006.01) | |
| *A61M 5/19* | (2006.01) | |
| *A61M 5/20* | (2006.01) | |
| *A61M 5/24* | (2006.01) | |

(Continued)

(52) U.S. Cl.
CPC .......... *A61M 5/31596* (2013.01); *A61M 5/19* (2013.01); *A61M 5/2033* (2013.01); *A61M 5/2466* (2013.01); *A61M 5/285* (2013.01); *A61M 5/14244* (2013.01);

(Continued)

(58) Field of Classification Search
CPC ................ A61M 5/286; A61M 5/2466; A61M 2005/1787; A61M 2005/2474; A61M 5/288

See application file for complete search history.

(56) References Cited

U.S. PATENT DOCUMENTS

| | | |
|---|---|---|
| 1,441,508 A | 1/1923 | Marius et al. |
| 2,198,666 A | 4/1940 | Gruskin |

(Continued)

FOREIGN PATENT DOCUMENTS

| | | |
|---|---|---|
| CA | 606281 A | 10/1960 |
| CN | 1375338 A | 10/2002 |

(Continued)

OTHER PUBLICATIONS

International Search Report and Written Opinion for PCT/US2018/014351, dated Jun. 4, 2018, 11 pages.

(Continued)

*Primary Examiner* — Emily L Schmidt

(57) ABSTRACT

A multi-stage drug delivery system having a cartridge and multiple plungers positioned in the cartridge and spaced apart from one another is provided. A first plunger, a second plunger, and the cartridge form a first chamber storing a first drug. The second plunger and the cartridge form a second chamber storing a second drug. A cannula pierces the first plunger to access the first drug. As the first plunger is driven toward the second plunger, the first drug is expelled from the first chamber for delivery to a patient through the cannula. After expelling the first liquid drug, the cannula can pierce the second plunger to access the second drug. As the first and second plungers are together driven toward a closed end of the cartridge, the second liquid drug is expelled from the second chamber for delivery to the patient through the cannula.

22 Claims, 8 Drawing Sheets

(51) Int. Cl.
*A61M 5/178* (2006.01)
*A61M 5/142* (2006.01)

(52) U.S. Cl.
CPC .............. *A61M 2005/1787* (2013.01); *A61M 2005/2474* (2013.01); *A61M 2205/0216* (2013.01)

(56) References Cited

U.S. PATENT DOCUMENTS

| | | |
|---|---|---|
| 3,176,712 A | 4/1965 | Ramsden |
| 3,297,260 A | 1/1967 | Barlow |
| 3,885,662 A | 5/1975 | Schaefer |
| 3,946,732 A | 3/1976 | Hurscham |
| 3,993,061 A | 11/1976 | O'Leary |
| 4,108,177 A | 8/1978 | Pistor |
| 4,152,098 A | 5/1979 | Moody et al. |
| 4,210,173 A | 7/1980 | Choksi et al. |
| 4,221,219 A | 9/1980 | Tucker |
| 4,257,324 A | 3/1981 | Stefansson et al. |
| 4,268,150 A | 5/1981 | Chen |
| 4,313,439 A | 2/1982 | Babb et al. |
| 4,417,889 A | 11/1983 | Choi |
| 4,424,720 A | 1/1984 | Bucchianeri |
| 4,435,173 A | 3/1984 | Siposs et al. |
| 4,498,843 A | 2/1985 | Schneider et al. |
| 4,507,115 A | 3/1985 | Kambara et al. |
| 4,551,134 A | 11/1985 | Slavik et al. |
| 4,562,751 A | 1/1986 | Nason et al. |
| 4,567,549 A | 1/1986 | Lemme |
| 4,585,439 A | 4/1986 | Michel |
| 4,601,707 A | 7/1986 | Albisser et al. |
| 4,634,427 A | 1/1987 | Hannula et al. |
| 4,671,429 A | 6/1987 | Spaanderman et al. |
| 4,678,408 A | 7/1987 | Nason et al. |
| 4,684,368 A | 8/1987 | Kenyon |
| 4,685,903 A | 8/1987 | Cable et al. |
| 4,755,169 A | 7/1988 | Sarnoff et al. |
| 4,766,889 A | 8/1988 | Trick et al. |
| 4,808,161 A | 2/1989 | Kamen |
| 4,846,797 A | 7/1989 | Howson et al. |
| 4,858,619 A | 8/1989 | Toth |
| 4,898,579 A | 2/1990 | Groshong et al. |
| 4,908,017 A | 3/1990 | Howson et al. |
| 4,944,659 A | 7/1990 | Labbe et al. |
| 4,969,874 A | 11/1990 | Michel et al. |
| 5,007,458 A | 4/1991 | Marcus et al. |
| 5,020,325 A | 6/1991 | Henault |
| 5,062,841 A | 11/1991 | Siegel |
| 5,178,609 A | 1/1993 | Ishikawa |
| 5,205,819 A | 4/1993 | Ross et al. |
| 5,213,483 A | 5/1993 | Flaherty et al. |
| 5,222,362 A | 6/1993 | Maus et al. |
| 5,236,416 A | 8/1993 | McDaniel et al. |
| 5,261,882 A | 11/1993 | Sealfon |
| 5,261,884 A | 11/1993 | Stern et al. |
| 5,277,338 A | 1/1994 | Divall |
| 5,281,202 A | 1/1994 | Weber et al. |
| 5,346,476 A | 9/1994 | Elson |
| 5,364,342 A | 11/1994 | Beuchat et al. |
| 5,388,615 A | 2/1995 | Edlund et al. |
| 5,433,710 A | 7/1995 | VanAntwerp et al. |
| 5,503,628 A | 4/1996 | Fetters et al. |
| 5,520,661 A | 5/1996 | Lal et al. |
| 5,533,389 A | 7/1996 | Kamen et al. |
| 5,582,593 A | 12/1996 | Hultman |
| 5,618,269 A | 4/1997 | Jacobsen et al. |
| 5,637,095 A | 6/1997 | Nason et al. |
| 5,665,070 A | 9/1997 | McPhee |
| 5,713,875 A | 2/1998 | Tanner, II |
| 5,747,350 A | 5/1998 | Sattler |
| 5,748,827 A | 5/1998 | Holl et al. |
| 5,776,103 A | 7/1998 | Kriesel et al. |
| 5,779,676 A | 7/1998 | Kriesel et al. |
| 5,785,688 A | 7/1998 | Joshi et al. |
| 5,797,881 A | 8/1998 | Gadot |
| 5,800,397 A | 9/1998 | Wilson et al. |
| 5,807,075 A | 9/1998 | Jacobsen et al. |
| 5,839,467 A | 11/1998 | Saaski et al. |
| 5,891,097 A | 4/1999 | Saito et al. |
| 5,897,530 A | 4/1999 | Jackson |
| 5,906,597 A | 5/1999 | McPhee |
| 5,911,716 A | 6/1999 | Rake et al. |
| 5,919,167 A | 7/1999 | Mulhauser et al. |
| 5,957,890 A | 9/1999 | Mann et al. |
| 5,961,492 A | 10/1999 | Kriesel et al. |
| 5,971,963 A | 10/1999 | Choi |
| 6,019,747 A | 2/2000 | McPhee |
| 6,050,457 A | 4/2000 | Arnold et al. |
| 6,159,188 A | 12/2000 | Laibovitz et al. |
| 6,174,300 B1 | 1/2001 | Kriesel et al. |
| 6,190,359 B1 | 2/2001 | Heruth |
| 6,200,293 B1 | 3/2001 | Kriesel et al. |
| 6,363,609 B1 | 4/2002 | Pickren |
| 6,375,638 B2 | 4/2002 | Nason et al. |
| 6,474,219 B2 | 11/2002 | Klitmose et al. |
| 6,485,461 B1 | 11/2002 | Mason et al. |
| 6,485,462 B1 | 11/2002 | Kriesel |
| 6,488,652 B1 | 12/2002 | Weijand et al. |
| 6,520,936 B1 | 2/2003 | Mann |
| 6,527,744 B1 | 3/2003 | Kriesel et al. |
| 6,537,249 B2 | 3/2003 | Kriesel et al. |
| 6,569,115 B1 | 5/2003 | Barker et al. |
| 6,595,956 B1 | 7/2003 | Gross et al. |
| 6,656,158 B2 | 12/2003 | Mahoney et al. |
| 6,699,218 B2 | 3/2004 | Flaherty et al. |
| 6,723,072 B2 | 4/2004 | Flaherty et al. |
| 6,749,407 B2 | 6/2004 | Xie et al. |
| 6,851,260 B2 | 2/2005 | Mernoe |
| 6,883,778 B1 | 4/2005 | Newton et al. |
| 7,018,360 B2 | 3/2006 | Flaherty et al. |
| 7,128,727 B2 | 10/2006 | Flaherty et al. |
| 7,144,384 B2 | 12/2006 | Gorman et al. |
| 7,160,272 B1 | 1/2007 | Eyal et al. |
| 7,771,392 B2 | 8/2010 | De Polo et al. |
| 7,914,499 B2 | 3/2011 | Gonnelli et al. |
| 8,382,703 B1 | 2/2013 | Abdelaal |
| 8,499,913 B2 | 8/2013 | Gunter |
| 8,939,935 B2 | 1/2015 | O'Connor et al. |
| 9,180,244 B2 | 11/2015 | Anderson et al. |
| 9,192,716 B2 | 11/2015 | Jugl et al. |
| 9,402,950 B2 | 8/2016 | Dilanni et al. |
| 2001/0016710 A1 | 8/2001 | Nason et al. |
| 2001/0056258 A1 | 12/2001 | Evans |
| 2002/0029018 A1 | 3/2002 | Jeffrey |
| 2002/0032374 A1 | 3/2002 | Holker et al. |
| 2002/0037221 A1 | 3/2002 | Mastrangelo et al. |
| 2002/0173769 A1 | 11/2002 | Gray et al. |
| 2002/0173830 A1 | 11/2002 | Starkweather et al. |
| 2003/0040715 A1 | 2/2003 | D'Antonio et al. |
| 2003/0097092 A1 | 5/2003 | Flaherty |
| 2003/0109827 A1* | 6/2003 | Lavi ................ A61M 5/14248 604/134 |
| 2003/0163097 A1 | 8/2003 | Fleury et al. |
| 2003/0199825 A1 | 10/2003 | Flaherty |
| 2004/0010207 A1 | 1/2004 | Flaherty et al. |
| 2004/0064088 A1 | 4/2004 | Gorman et al. |
| 2004/0068224 A1 | 4/2004 | Couvillon, Jr. et al. |
| 2004/0069044 A1 | 4/2004 | Lavi et al. |
| 2004/0092865 A1 | 5/2004 | Flaherty et al. |
| 2004/0094733 A1 | 5/2004 | Hower et al. |
| 2004/0153032 A1 | 8/2004 | Garribotto et al. |
| 2005/0020980 A1 | 1/2005 | Inoue et al. |
| 2005/0203461 A1 | 9/2005 | Flaherty et al. |
| 2005/0238507 A1 | 10/2005 | Dilanni et al. |
| 2005/0273059 A1 | 12/2005 | Mernoe et al. |
| 2006/0041229 A1 | 2/2006 | Garibotto et al. |
| 2006/0079765 A1 | 4/2006 | Neer |
| 2006/0155210 A1 | 7/2006 | Beckman et al. |
| 2006/0173439 A1* | 8/2006 | Thorne, Jr. ....... A61M 5/14244 604/506 |
| 2006/0178633 A1 | 8/2006 | Garibotto et al. |
| 2006/0253085 A1 | 11/2006 | Geismar et al. |
| 2006/0282290 A1 | 12/2006 | Flaherty et al. |
| 2007/0005018 A1 | 1/2007 | Tekbuchava |

(56) References Cited

U.S. PATENT DOCUMENTS

| | | | |
|---|---|---|---|
| 2007/0118405 | A1 | 5/2007 | Campbell et al. |
| 2007/0282269 | A1 | 12/2007 | Carter et al. |
| 2008/0004515 | A1 | 1/2008 | Jennewine |
| 2008/0051738 | A1 | 2/2008 | Griffin |
| 2008/0114304 | A1 | 5/2008 | Nalesso et al. |
| 2008/0172028 | A1 | 7/2008 | Blomquist |
| 2009/0024083 | A1 | 1/2009 | Kriesel et al. |
| 2009/0062767 | A1 | 3/2009 | Van Antwerp et al. |
| 2009/0198215 | A1 | 8/2009 | Chong et al. |
| 2010/0036326 | A1 | 2/2010 | Matusch |
| 2010/0152658 | A1 | 6/2010 | Hanson et al. |
| 2010/0241066 | A1 | 9/2010 | Hansen et al. |
| 2011/0054399 | A1 | 3/2011 | Chong et al. |
| 2011/0144586 | A1 | 6/2011 | Michaud et al. |
| 2011/0230833 | A1 | 9/2011 | Landman et al. |
| 2012/0078161 | A1 | 3/2012 | Masterson et al. |
| 2013/0006213 | A1* | 1/2013 | Arnitz ............ A61M 5/14248 604/414 |
| 2013/0017099 | A1 | 1/2013 | Genoud et al. |
| 2013/0064701 | A1 | 3/2013 | Konishi |
| 2013/0245545 | A1 | 9/2013 | Arnold et al. |
| 2013/0267932 | A1* | 10/2013 | Franke ............ A61M 5/2448 604/506 |
| 2014/0018730 | A1 | 1/2014 | Muller-Pathle |
| 2014/0127048 | A1 | 5/2014 | Dilanni et al. |
| 2014/0128839 | A1 | 5/2014 | Dilanni et al. |
| 2014/0142508 | A1 | 5/2014 | Dilanni et al. |
| 2014/0148784 | A1* | 5/2014 | Anderson ......... A61M 5/14248 604/506 |
| 2014/0171901 | A1 | 6/2014 | Langsdorf et al. |
| 2015/0041498 | A1 | 2/2015 | Kakiuchi et al. |
| 2015/0057613 | A1* | 2/2015 | Clemente ......... A61M 5/14566 604/148 |
| 2015/0081337 | A1 | 3/2015 | Luce |
| 2015/0202386 | A1 | 7/2015 | Brady et al. |
| 2015/0290389 | A1 | 10/2015 | Nessel |
| 2015/0297825 | A1 | 10/2015 | Focht et al. |
| 2016/0025544 | A1 | 1/2016 | Kamen et al. |
| 2016/0193423 | A1 | 7/2016 | Bilton |
| 2017/0021096 | A1 | 1/2017 | Cole et al. |
| 2017/0021137 | A1 | 1/2017 | Cole |
| 2017/0216516 | A1 | 8/2017 | Dale et al. |
| 2017/0239415 | A1 | 8/2017 | Hwang et al. |
| 2018/0313346 | A1 | 11/2018 | Oakes et al. |

FOREIGN PATENT DOCUMENTS

| | | |
|---|---|---|
| DE | 4200595 A1 | 7/1993 |
| DE | 19723648 C1 | 8/1998 |
| EP | 0454331 A1 | 10/1991 |
| EP | 0789146 A1 | 8/1997 |
| EP | 867196 A2 | 9/1998 |
| EP | 1065378 A2 | 1/2001 |
| EP | 1177802 A1 | 2/2002 |
| EP | 1403519 A1 | 3/2004 |
| EP | 2397181 A1 | 12/2011 |
| EP | 2468338 A1 | 6/2012 |
| EP | 2703024 A1 | 3/2014 |
| EP | 2830499 A1 | 2/2015 |
| FR | 2096275 A5 | 2/1972 |
| FR | 2455269 A1 | 11/1980 |
| FR | 2507637 A1 | 12/1982 |
| FR | 2731475 A1 | 9/1996 |
| GB | 357139 A | 9/1931 |
| GB | 810488 A | 3/1959 |
| GB | 875034 A | 8/1961 |
| GB | 1204836 A | 9/1970 |
| GB | 2008806 A | 6/1979 |
| GB | 2077367 A | 12/1981 |
| GB | 2456681 A | 7/2009 |
| GB | 2549750 A | 11/2017 |
| IL | 46017 A | 11/1977 |
| JP | 06063133 A | 3/1994 |
| JP | 6098988 B2 | 4/1994 |
| JP | H08238324 A | 9/1996 |
| JP | 2004247271 A | 9/2004 |
| JP | 2004274719 A | 9/2004 |
| JP | 2005188355 A | 7/2005 |
| JP | 2006159228 A | 6/2006 |
| JP | 2006249130 A | 9/2006 |
| NL | 1019126 C1 | 4/2003 |
| WO | 8101658 A1 | 6/1981 |
| WO | 8606796 A1 | 11/1986 |
| WO | 9415660 A1 | 7/1994 |
| WO | 9855073 A1 | 12/1998 |
| WO | 9856293 A1 | 12/1998 |
| WO | 9910040 A1 | 3/1999 |
| WO | 9910049 A1 | 3/1999 |
| WO | 9962576 A1 | 12/1999 |
| WO | 0029047 A1 | 5/2000 |
| WO | 0178812 A1 | 10/2001 |
| WO | 0220073 A2 | 3/2002 |
| WO | 0226282 A2 | 4/2002 |
| WO | 02068823 A1 | 9/2002 |
| WO | 02076535 A1 | 10/2002 |
| WO | 2003097133 A1 | 11/2003 |
| WO | 2004056412 A2 | 7/2004 |
| WO | 2004110526 A1 | 12/2004 |
| WO | 2007066152 A2 | 6/2007 |
| WO | 2008133702 A1 | 11/2008 |
| WO | 2009039203 A2 | 3/2009 |
| WO | 2010139793 A1 | 12/2010 |
| WO | 2011075042 A1 | 6/2011 |
| WO | 2011133823 A1 | 10/2011 |
| WO | 2012073032 A1 | 6/2012 |
| WO | 2013050535 A2 | 4/2013 |
| WO | 2013137893 A1 | 9/2013 |
| WO | 2013149186 A1 | 10/2013 |
| WO | 2014149357 A1 | 9/2014 |
| WO | 2015032772 A1 | 3/2015 |
| WO | 2015117854 A1 | 8/2015 |
| WO | 2015167201 A1 | 11/2015 |
| WO | 2015177082 A1 | 11/2015 |
| WO | 2017187177 A1 | 11/2017 |

OTHER PUBLICATIONS

Lind, et al., "Linear Motion Miniature Actuators." Paper presented at the 2nd Tampere International Conference on Machine Automation, Tampere, Finland (Sep. 1998).

Author unknown, "The Animas R-1000 Insulin Pump—Animas Corporation intends to exit the insulin pump business and discontinue the manufacturing and sale of Animas® Vibe® and OneTouch Ping® insulin pumps." [online], Dec. 1999 [retrieved on Jan. 8, 2019]. Retrieved from the Internet URL: http://www.animaspatientsupport.com/.

Author unknown, CeramTec "Discover the Electro Ceramic Products CeramTec acquired from Morgan Advanced Materials" [online], Mar. 1, 2001 [retrieved on Jan. 8, 2019. Retrieved from the Internet URL: http://www.morgantechnicalceramics.com/.

Vaughan, M.E., "The Design, Fabrication, and Modeling of a Piezoelectric Linear Motor." Master's thesis, Virginia Polytechnic Institute and State University, VA. (2001).

Galante, et al., "Design, Modeling, and Performance of a High Force Piezoelectric Inchworm Motor," Journal of Intelligent Material Systems and Structures, vol. 10, 962-972 (1999).

International Search Report and Written Opinion for Interantional application No. PCT/US2017/055054, dated Jan. 25, 2018, 16 pages.

International Search Report and Written Opinion for International application No. PCT/US2018/045155, dated Oct. 15, 2018, 15 pages.

International Preliminary Report on Patentability for International application No. PCT/US2017/034811 dated Nov. 27, 2018 10 pages.

International Search Report and Written Opinion for International application No. PCT/US2017/046508, dated Jan. 17, 2018, 16 pages.

International Search Report and Written Opinion for International application No. PCT/US2017/046777, dated Dec. 13, 2017, 16 pages.

(56) References Cited

OTHER PUBLICATIONS

International Search Report and Written Opinion for International application No. PCT/US2017/046737, dated Dec. 14, 2017, 13 pages.
International Search Report and Written Opinion for application No. PCT/US2017/34814, dated Oct. 11, 2017, 16 pages.
International Preliminary Report on Patentability for the International Patent Application PCT/US2018/045155, dated Feb. 13, 2020, 10 pages.
International Search Report and Written Opinion for the International Patent Application No. PCT/GB2007/004073, dated Jan. 31, 2008, 8 pages.
European Search Report and Written Opinion for the European Patent Application No. EP19177571, dated Oct. 30, 2019, 10 pages.
International Search Report and Written Opinion for the International Patent Application No. PCT/US2019/035756, dated Jul. 31, 2019, 11 pages.
International Preliminary Report on Patentability for the International Patent Application No. PCT/US18/14351, dated Aug. 1, 2019, 6 pages.
International Preliminary Report on Patentability for the International Patent Application No. PCT/US2017/046777, dated Feb. 28, 2019, 8 pages.
International Preliminary Report on Patentability for the International Patent Application No. PCT/US2017/046737, dated Feb. 28, 2019, 8 pages.
International Preliminary Report on Patentability for the International Patent Application No. PCT/US2017/046508, dated Feb. 21, 2019, 10 pages.
International Preliminary Report on Patentability for the International Patent Application No. PCT/US2017/055054, dated Apr. 18, 2019, 8 pages.
International Search Report and Written Opinion for the International Patent Application No. PCT/US13/34674, dated Aug. 6, 2013, 19 pages.
EPO Search Report for Application No. 13768938.6, dated Nov. 11, 2015, 7 pages.
International Search Report and Written Opinion for the International Patent Application No. PCT/US2019/063615, dated May 3, 2020, 17 pages.

* cited by examiner

MULTI-STAGE DELIVERY SYSTEM

CROSS-REFERENCE TO RELATED APPLICATIONS

This application claims the benefit of U.S. Provisional Application No. 62/405,489, filed Oct. 7, 2016, which is incorporated herein by reference in its entirety.

TECHNICAL FIELD

Embodiments generally relate to medication delivery. More particularly, embodiments relate to drug delivery systems for delivering multiple different drugs.

BACKGROUND

Many patients may be required to receive dosages of different drugs. Conventional drug delivery systems, such as many conventional wearable drug delivery devices, typically only provide a dosage of a single drug. Therefore, a patient may be required to use multiple conventional drug delivery devices to receive the different drug dosages. With each additional device, the patient is required to insert a new needle to facilitate delivery of each drug. Accordingly, what is needed is a drug delivery system that can deliver multiple different drugs and dosages in a less burdensome manner while reducing patient discomfort.

DETAILED DESCRIPTION

This disclosure presents various systems, components, and methods related to a drug delivery system. Each of the systems, components, and methods disclosed herein provides one or more advantages over conventional systems, components, and methods.

Various embodiments provide a multiple stage (multi-stage) drug delivery system and method of use. The multi-stage drug delivery system can include two or more chambers for storing liquid drugs. The multi-stage drug delivery system can deliver each drug to a user in succession. The multi-stage drug delivery system can include the same drugs or different drugs. The multi-stage drug delivery system can store and dispense the same amount of each drug or different amounts of each drug. Each drug can be delivered at a desired rate over a desired amount of time. The multi-stage drug delivery system can interface with a variety of different fluid delivery mechanisms to pass the stored drugs to the user. The multi-stage drug delivery system provides a simplified architecture for storing and dispensing multiple different drugs to the user within the same container, enabling the user to use a same needle insertion to deliver the drugs. The multi-stage drug delivery device can be implemented within an on-body or wearable drug delivery device. Other embodiments are disclosed and described.

Various embodiments include a multi-stage drug delivery system having a cartridge, a first plunger positioned in the cartridge, and a second plunger positioned in the cartridge with the second plunger spaced apart from the first cartridge. The first plunger can be accessible through a first end of the cartridge. The first plunger, the second plunger, and the cartridge can form a first chamber configured to store a first liquid drug. The second plunger and the cartridge can form a second chamber configured to store a second liquid drug. A cannula can pierce the first plunger to access the first liquid drug. As the first plunger is driven toward the second plunger, the first liquid drug can be expelled from the first chamber for delivery to a patient through the cannula. After expelling the first liquid drug, the cannula can pierce the second plunger to access the second liquid drug. As the first and second plungers are together driven toward a closed end of the cartridge, the second liquid drug can be expelled from the second chamber for delivery to the patient through the cannula. The multi-stage drug delivery system allows two or more drugs to be delivered to a patient at different predetermined times, in different amounts, and according to different rates.

Figure 1:
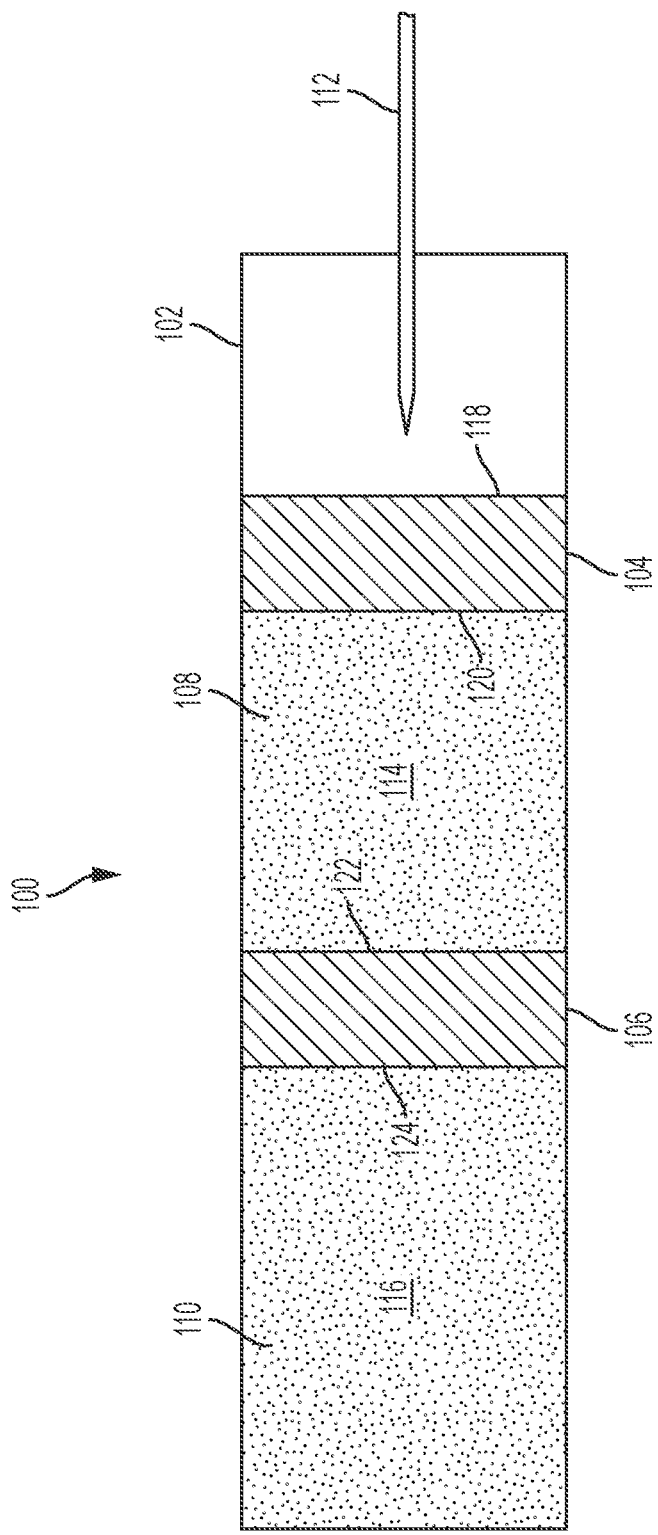
FIG. 1 illustrates an exemplary multiple stage (multi-stage) drug delivery system.

FIG. 1 illustrates a multi-stage drug delivery system 100. The multi-stage drug delivery system 100 can include a cartridge 102, a first plunger 104, and a second plunger 106. The multi-stage drug delivery system 100 can further include a first drug 108 and a second drug 110. The first and second drugs 108 and 110 can be any therapeutic agent including liquid drugs. The first and second drugs 108 and 110 can be different therapeutic agents or drugs. The multi-stage drug delivery system 100 can separately store and dispense the first and second drugs 108 and 110 using a common or shared drug delivery mechanism while enabling each drug to be dispensed at different times according to different customized schedules (e.g., different rates of delivery). The cartridge 102 can be of any size or shape. As an example, the cartridge 102 can be cylindrical with a circular cross-sectional shape.

As shown in FIG. 1, the first drug 108 can be stored in a first chamber 114 defined by the first plunger 104, the second plunger 106, and the cartridge 102. The storage and use of the first drug 108 in the first chamber 114 can represent a first stage of the multi-stage drug delivery system 100. The second drug 110 can be stored in a second chamber 116 defined by the second plunger 106 and the cartridge 102. The storage and use of the second drug 110 in the second chamber 116 can represent a second stage of the multi-stage drug delivery system 100.

The first and second drugs 108 and 110 can be hermetically separated and sealed by the cartridge 102 and the first and second plungers 104 and 106 as shown in FIG. 1. The first and second plungers 104 and 106 can be elastomeric plungers. The first and second drugs 108 and 110 can be provided in a common device (e.g., the cartridge 102) while ensuring the first and second drugs 108 and 110 are separately stored and dispensed. The first and second plungers 104 and 106 can be positioned anywhere along an interior portion of the cartridge 102.

The multi-stage drug delivery system 100 can be used in a drug delivery device that provides the first and second drugs 108 and 110 to a user. For example, the multi-stage drug delivery system 100 can be part of a bolus device and/or a wearable drug delivery device. The multi-stage drug delivery system 100 can include the same or different amounts of the first and second drugs 108 and 110 (e.g., the dosages of the first and second drugs 108 and 110 can be the same or different). The first drug 108 can be dispensed first over a first amount of time at a first rate of delivery with the second drug 110 dispensed over a second amount of time at a second rate of delivery, after the first drug 108 is dispensed. The multi-stage drug delivery system 100 enables the first and second drugs 108 and 110 to be provided to the user using the same fluid path to the user. Consequently, a single needle insertion can be used to deliver the first and second drugs 108 and 110.

The multi-stage drug delivery system 100 can dispense the second drug 110 immediately after the first drug 108 has been dispensed or can deliver the second drug 110 after a delay. Accordingly, the first and second drugs 108 and 110 can be delivered relatively close together in time or can be delivered at separate times after a desired delay. Further, the delivery of the first and second drugs 108 and 110 can be customized in terms of the rate at which each drug is delivered. For example, the first drug 108 can be delivered over a first amount of time while the second drug can be delivered over a second, different amount of time. The first and second amounts of time can be varied as desired to dispense the first and second drugs 108 and 110 at different desired rates of delivery, respectively. In this way, a customized delivery of the first and second drugs 108 and 110 can be provided with the dosages (e.g., how much drug to dispense in total), delivery times (e.g., when to dispense a drug), and delivery schedules (e.g., how quickly or slowly to dispense the dosage) for each drug being largely independent of each another.

FIG. 1 shows the multi-stage drug delivery system 100 in an initial state. Specifically, no mechanical energy or force is introduced or applied to the multi-stage drug delivery system 100 as shown in FIG. 1. A cannula 112 is shown in relatively close proximity to the multi-stage drug delivery system 100. The cannula 112 can be a hard cannula 112 that is sterilized. The cannula 112 can be positioned adjacent to the cartridge 102 or within an open area of the cartridge 102 yet still displaced from the first plunger 104. The cannula 112 can initially be positioned entirely outside of the cartridge 102. FIG. 1 can represent the multi-stage drug delivery system 100 before activation (e.g., before activation of a wearable drug delivery device in which the multi-stage drug delivery system 100 operates).

As shown in FIG. 1, the cannula 112 can be positioned adjacent to a first end of the cartridge 102. In particular, the cannula 112 is positioned in proximity to a first surface 118 of the first plunger 104. The first surface 118 can be adjacent to an open end of the cartridge 102 which allows the cannula 112 to enter the cartridge 102. The first plunger 104 can further include a second surface 120. The second surface 120 can be adjacent to the first drug 108. The second plunger 106 can also include a first surface 122 and a second surface 124. The first surface 122 can be adjacent to the first drug 108 and the second surface 124 can be adjacent to the second drug 110 as shown.

Figure 2:
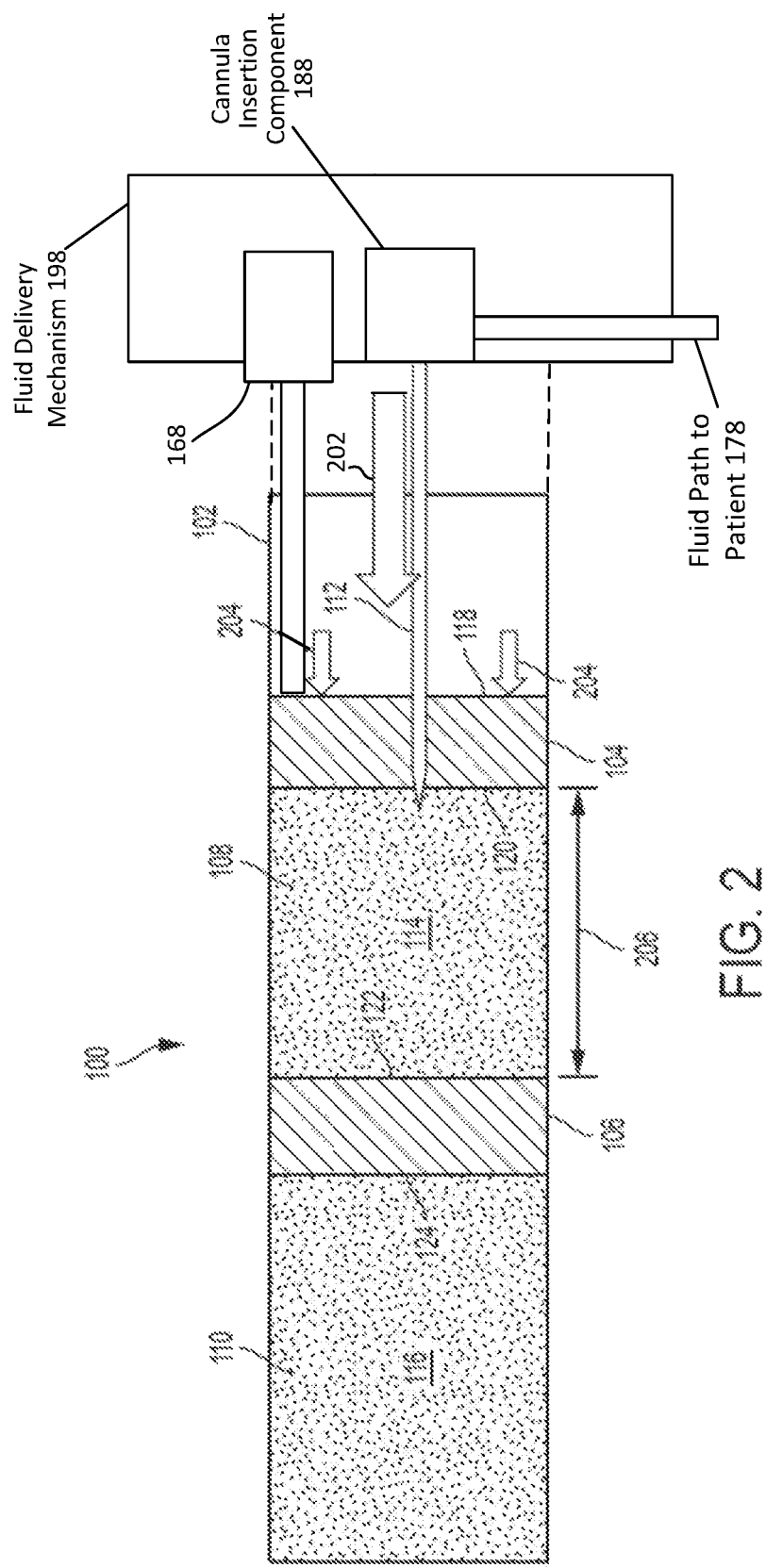
FIG. 2 illustrates the multi-stage drug delivery system of FIG. 1 in a first stage of operation.

FIG. 2 illustrates insertion of the cannula 112 into the first stage of the multi-stage drug delivery system 100 (e.g., into the first chamber 114). As shown in FIG. 2, indicator 202 indicates application of a force applied to the cannula 112. The application of the force 202 to the cannula 112 can cause the cannula 112 to pierce and pass through the first plunger 104. The force 202 can be such that the cannula 112 pierces through the first plunger 104 to enter the first stage (e.g., the first chamber 114) holding the first drug 108. The force 202 can cause the cannula to enter the first chamber 114 at a desired depth. For example, the cannula 112 can pierce the first plunger 104 and enter the first stage at a depth so as to maximize extraction of the first drug 108 stored in the first chamber 114. In various embodiments, the body of the first plunger 104 may be counter-bored to facilitate piercing by the cannula 112.

As shown in FIG. 2, to enter the first chamber 114 holding the first drug 108, the cannula 112 can be caused to pierce the first surface 118 and the second surface 120 of the first plunger 104 and to extend through the first plunger 104. A tip or end or the cannula 112 can be sharp or pointed to facilitate piercing of the first plunger 104. To obtain access to the first chamber 114, the cannula 112 can be caused to move in a lateral direction toward a far end of the cartridge 102 as shown. The tip or end of the cannula 112 can be positioned near to the second surface 120 of the first plunger 104 once access to the first chamber 114 is provided. The cannula 112 can be positioned at a center of the first plunger 104 but is not so limited. In various embodiments, the first plunger 114 can be inserted along any portion of the first surface 118 of the first plunger 104 for example.

Once the cannula 112 is inserted into the first stage of the multi-stage drug delivery system 100 at a desired depth, the first drug 108 can be introduced into the fluid delivery mechanism coupled to the cannula 112. As an example, the cannula 112 can be coupled to a fluid delivery mechanism that delivers the first drug 108 to a user or patient. A variety of fluid delivery mechanisms can be used. For example, the fluid delivery mechanism can include one or more components for coupling the cannula 112 to the patient. In various embodiments, the components can include tubing (e.g., plastic and/or stainless steel tubing) coupled to the cannula as well as a needle or cannula (e.g., coupled to the tubing) for accessing a site on the patient. Overall, the fluid delivery mechanism 198 can be or can provide a fluid path 178 from the cannula to the user of the multi-stage drug delivery system 100. Accordingly, when the cannula 112 is coupled to a liquid drug, then the fluid path can be used to deliver the liquid drug to the user. In various embodiments, the cannula 112 can be part of the fluid delivery mechanism 198 or can be coupled to it. In various embodiments, the cannula 112 can be coupled via the fluid path 178 to the patient.

The fluid delivery mechanism 198 can further be used to apply the force 202. As an example, the fluid delivery mechanism 198 can include a cannula insertion component 188 for driving the cannula 112 in a direction indicated by the applied force 202 to pierce the first plunger 104. The cannula insertion component 188 can be coupled to the cannula 112 and can be triggered to cause the cannula 112 to advance toward the first plunger 104 to pierce the first plunger 104. In various embodiments, the cannula insertion component 188 can comprise a mechanical system or an electromechanical system for manipulating the cannula 112. In various embodiments, the cannula insertion component 188 can include one or more springs such as, for example, an expansion spring, a compression spring, and/or a torsion spring. The cannula insertion component 188 can be triggered to pierce the cannula 112 through the first plunger 104 based on a user input or action that indicates a desire to activate delivery of the first drug 108 (e.g., by a user pressing a button on a wearable drug delivery device to activate the device).

Further, the fluid delivery mechanism 198 can include a drive component, such as 168, to apply a force 204 on the first plunger 104 to force the first drug 108 out of the first stage of the multi-stage drug delivery system 100. For example, after the cannula 112 pierces the first plunger 104 and is positioned at a desired depth within the first chamber 114, a second force can be applied to the first plunger 104 as indicated by indicators 204. The force 204 can be applied to any portion of the first surface 118 of the first plunger 104 (e.g., at one or more positions along the first surface 118). The force 204 can drive the first drug 108 out of the first chamber 114, through the fluid delivery mechanism 198 (e.g., the cannula 112 and any other components coupling the cannula to the patient), and on to the user. The force 204 can cause the first plunger 104 to move towards the stationary second plunger 106. The drive component 168 can be coupled to the first plunger 104. In various embodiments, the drive component 168 can comprise a mechanical system or an electromechanical system for driving the first plunger 104 toward the far end of the cartridge 102. In various embodiments, the drive component 168 can include one or more springs such as, for example, an expansion spring, a compression spring, and/or a torsion spring.

The applied force 204 can be constant or varied and can be used to deliver the first drug 108 to the user over a desired amount of time (e.g., at a desired rate of delivery). For example, a relatively strong force 204 can be applied to rapidly provide the first drug 108 to the user. Alternatively, a relatively weak force 204 can be applied to slowly provide the first drug 108 to the user. In general, any delivery schedule and rate of delivery of the first drug 108 can be provided by using and varying the force 204.

FIG. 2 also shows a stroke 206 of the multi-stage drug delivery system 100—that is, the distance the first plunger 104 travels to expel all or approximately all of the first drug 108 from the first chamber 114 of the multi-stage drug delivery system 100 (e.g., the stroke 206 can represent the amount of the first drug 108 that can be stored and provided to a user). As discussed above, the stroke 206 can be varied by the amount of the first drug 108 included in the multi-stage drug delivery system 100 and the magnitude and timing of the force 204 applied to the first plunger 104 can determine how the amount of the first drug 108 is provided to the user. FIG. 2 can represent a state of the multi-stage drug delivery system 100 when the first drug 108 is initially accessed (e.g., when the cannula 112 is first introduced into the first chamber 114). FIG. 2 can represent the multi-stage drug delivery system 100 after activation and as delivery of the first drug 108 to the user first begins.

Figure 3:
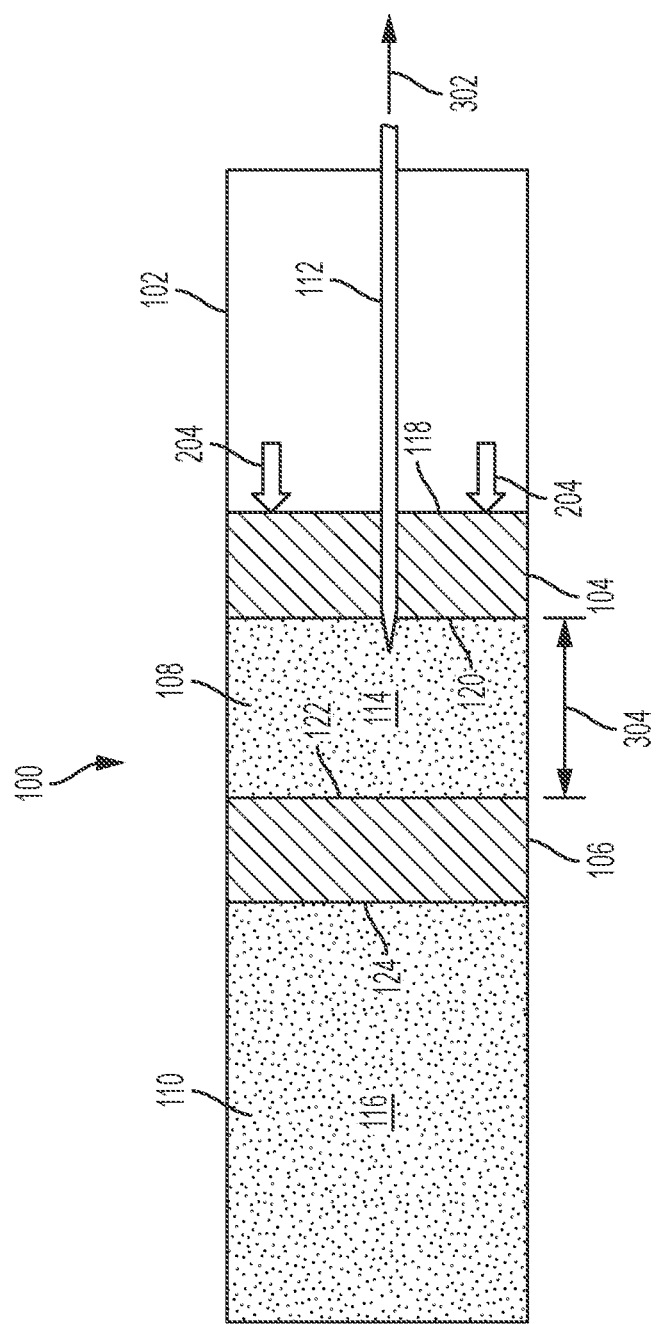
FIG. 3 illustrates the multi-stage drug delivery system of FIG. 1 in a second stage of operation.

FIG. 3 illustrates extraction of the first drug 108 from the multi-stage drug delivery system 100. Specifically, FIG. 3 shows the first plunger 104 being driven towards the second plunger 106. The second plunger 106 can be in a fixed position. As a result, the first drug 108 can be forced out of the first chamber 114 of the multi-stage drug delivery system 100, through the cannula 112, and on to the fluid delivery mechanism 198 coupled to the cannula 112 for delivery to the user. As shown in FIG. 3, indicator 302 represents the first liquid drug 108 from the first chamber 114 being expelled out of the first chamber 114 through the cannula 112. The first liquid drug 108 can flow out of the cartridge 102 in a direction that is substantially opposite to the direction of the movement of the first plunger 104 towards the second plunger 106 which causes the first liquid drug 108 to be expelled out of the first chamber 114.

As shown in FIG. 3, the force 204 can be applied to the first plunger 104 to drive it towards the second plunger 106. The inserted position of the cannula 112 can remain in relatively the same position with respect to the first plunger 104 to ensure maximize extraction of the first drug 108. A reduction in stroke 304 is also shown for reference in FIG. 3. The reduction in stroke 304 can indicate that the size of the first chamber 114 of the multi-stage drug delivery system 100 has been reduced and that a corresponding amount of the first drug 108 has exited the multi-stage drug delivery system 100 through the cannula 112 for delivery to the user. FIG. 3 can represent a state of the multi-stage drug delivery system 100 when the first drug 108 is being extracted.

Figure 4:
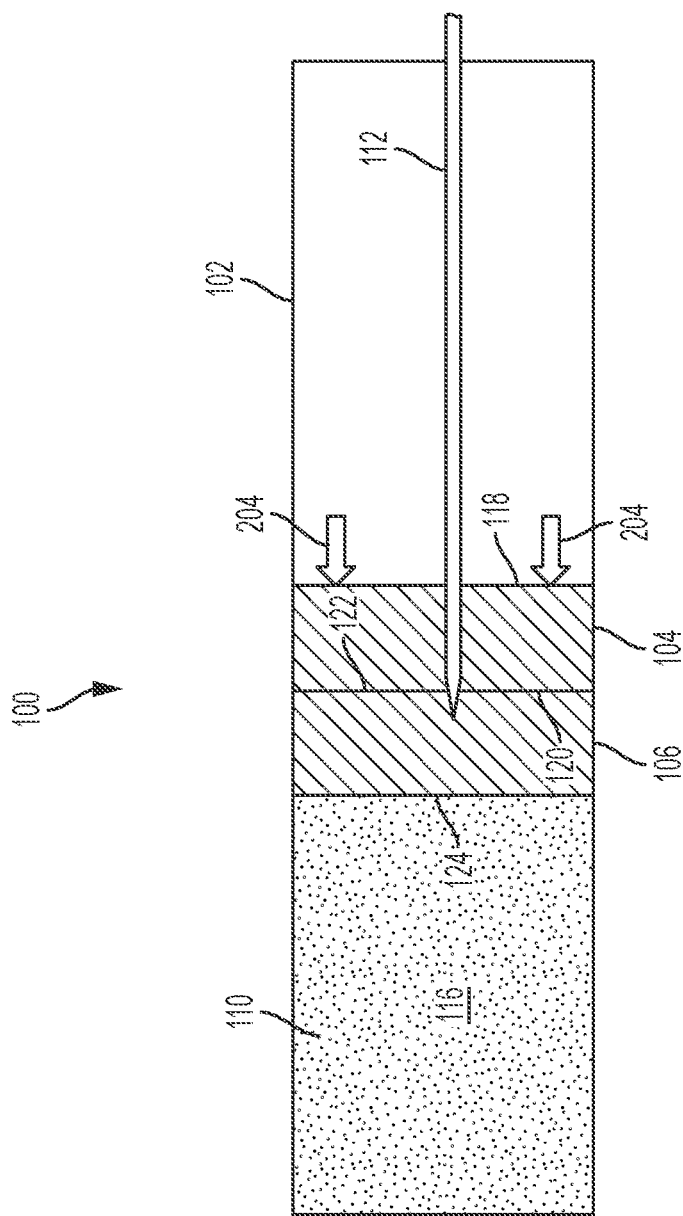
FIG. 4 illustrates the multi-stage drug delivery system of FIG. 1 in a third stage of operation.

FIG. 4 illustrates the multi-stage drug delivery system 100 after depletion of the first drug 108. That is, FIG. 4 shows the multi-stage drug delivery system 100 after all or approximately all of the first drug 108 has been extracted from the first chamber 114 of the multi-stage drug delivery system 100. As shown in FIG. 4, the first plunger 104 is in close proximity to the second plunger 106 (e.g., adjacent such that no portion of the first drug 108 remains between the first and second plungers 104 and 106). The second surface 120 of the first plunger 104 can be adjacent to or pressed against the first surface 122 of the second plunger 106.

The force 204 applied to the first plunger 104 can drive the first plunger 104 to the position shown in FIG. 4. As the first drug 108 is being depleted and as the first plunger 104 is forced against the second plunger 106, the cannula 112 can be introduced into the second plunger 106. As shown in FIG. 4, a portion of the end of the cannula 112 can pierce a portion of the second plunger 106. The cannula 112 can pierce the first surface 122 of the second plunger 106 and can be partially inserted into the second plunger 106. The state of the multi-stage drug delivery system 100 as shown in FIG. 4 can be a state following depletion of the first drug 108 and prior to extraction of the second drug 110.

Figure 5:
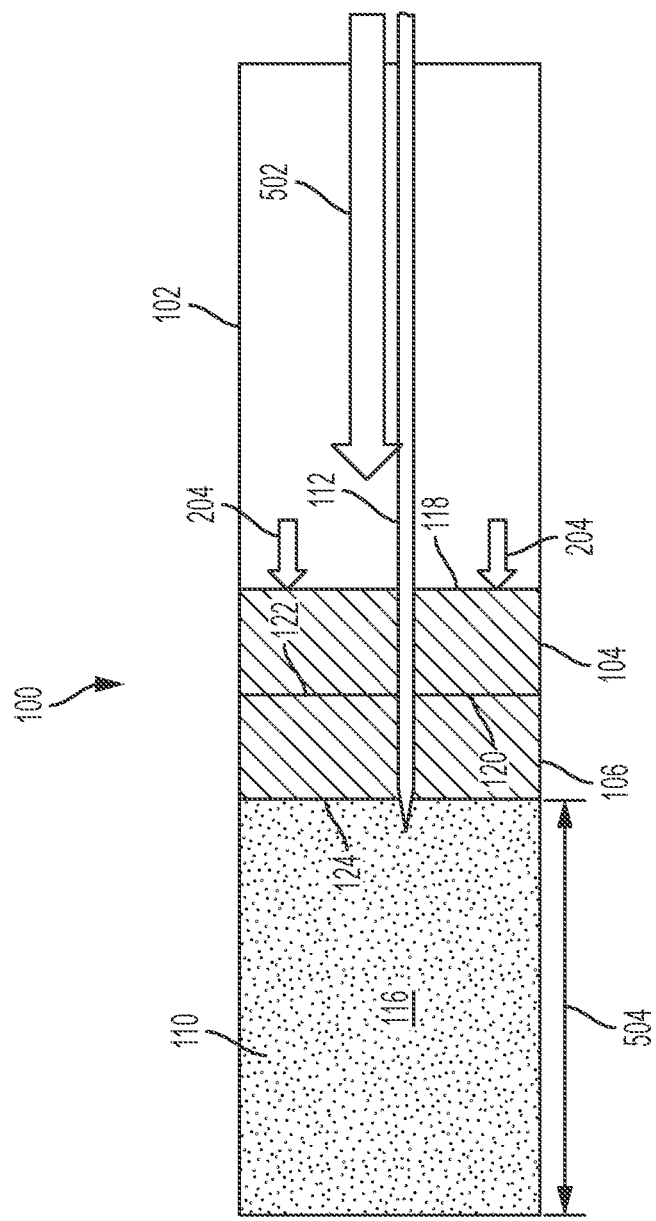
FIG. 5 illustrates the multi-stage drug delivery system of FIG. 1 in a fourth stage of operation.

FIG. 5 illustrates insertion of the cannula 112 through the second plunger 106 of the multi-stage drug delivery system 100 and into the second chamber 116. As shown in FIG. 5, a second force 502 can be applied to the cannula 112 to drive the cannula 112 through the second plunger 106. The end of the cannula 112 can extend into the second chamber 116 of the multi-stage drug delivery system 100 a desired amount to ensure maximum extraction of the second drug 110. The cannula 112 can extend beyond the second surface 124 of the second plunger to be coupled to the second liquid drug 110 stored in the second chamber 116.

When the cannula 112 is inserted through the second plunger 106 and into the second chamber 116 of the multi-stage drug delivery system 100, the second drug 110 can be introduced into the fluid path coupled to the user (e.g., a fluid path coupled to the cannula 112). Specifically, the second drug 110 can be provided to the delivery mechanism coupled to the cannula 112 so that the second drug 110 may be passed on to the user. As shown, the force 204 can be applied to the first plunger 104 to move both the first plunger 104 and the second plunger 106 toward the end of the cartridge 102. That is, by applying the force 204 to the first plunger 104, the second plunger 106 is forced to move toward an end of the cartridge 102. In turn, the volume or size of the second chamber 116 is reduced which forces the second drug 110 through the cannula 112 and on to the fluid delivery mechanism.

FIG. 5 also shows a stroke 504 for the second chamber 116 of the multi-stage drug delivery system 100—that is, the distance the second plunger 106 travels to expel all or approximately all of the second drug 110 from the second chamber 116 of the multi-stage drug delivery system 100 (e.g., the amount of the second drug 110 that can be stored and provided to a user). As discussed above, the stroke 504 can be varied by the amount of the second drug 110 included in the multi-stage drug delivery system 100 and the magnitude and timing of the force 204 applied to the first plunger 104 (and the second plunger 106) can determine how the amount of the second drug 110 is provided to the user. FIG. 5 can represent a state of the multi-stage drug delivery system 100 when the second drug 110 is initially accessed (e.g., when the cannula 112 is first introduced into the second chamber).

Figure 6:
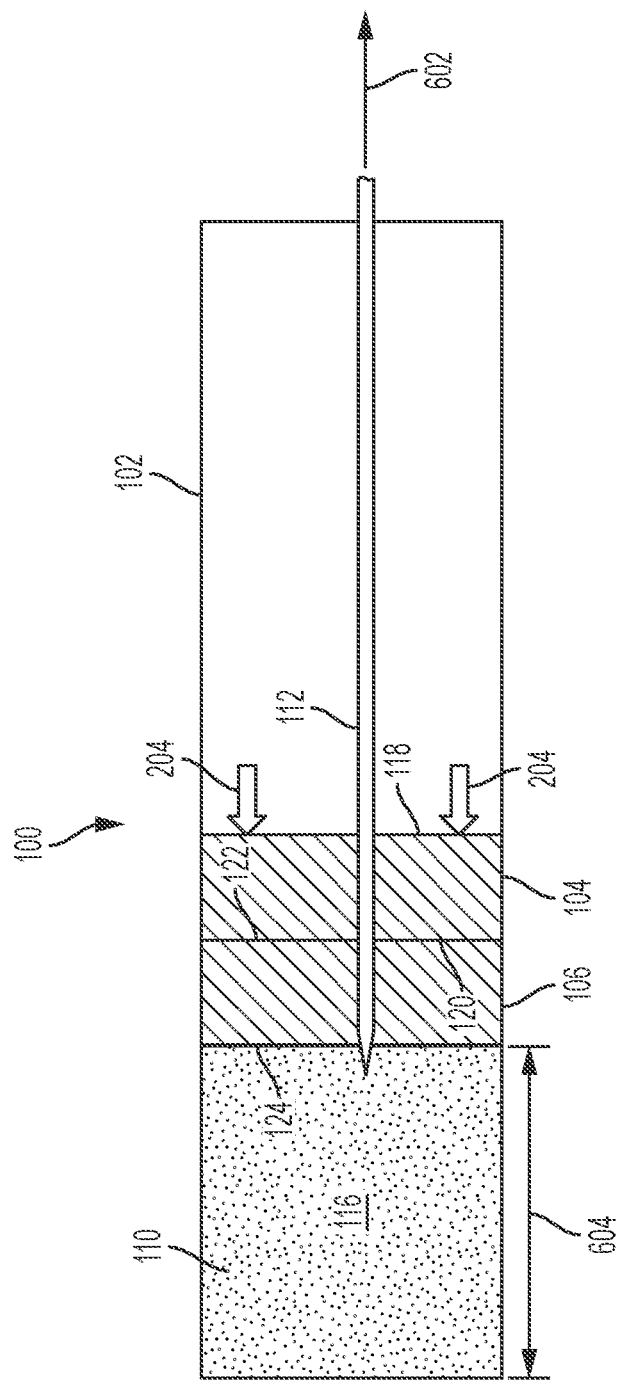
FIG. 6 illustrates the multi-stage drug delivery system of FIG. 1 in a fifth stage of operation.

FIG. 6 illustrates extraction of the second drug 110 from the multi-stage drug delivery system 100. Specifically, FIG. 6 shows the first plunger 104 and the second plunger 106 together being driven toward the end of the cartridge 102. As a result, the second drug 110 can be forced out of the second chamber 116 of the multi-stage drug delivery system 100, through the cannula 112, and on to the fluid delivery mechanism coupled to the cannula 112 for delivery to the user. As shown in FIG. 6, the force 204 can be applied to the first plunger 104 (and to the second plunger 106 indirectly) to drive both the first and second plungers 104 and 106 towards the end of the cartridge 102. The inserted position of the cannula 112 can remain in relatively the same position with respect to the second plunger 106 to ensure maximize extraction of the second drug 110.

As shown in FIG. 6, indicator 602 represents the second liquid drug 110 from the second chamber 116 being expelled out of the second chamber 116 through the cannula 112. The second liquid drug 110 can flow out of the cartridge 102 in a direction that is substantially opposite to the direction of the movement of the first plunger 104 and the second plunger 106 towards the end of the cartridge 102 which causes the second liquid drug 110 to be expelled out of the second chamber 116.

A reduction in stroke 604 is also shown for reference in FIG. 6—for example, to indicate the second chamber 116 of the multi-stage drug delivery system 100 has been reduced and that a corresponding amount of the second drug 110 has exited the multi-stage drug delivery system 100 for delivery to the user.

FIG. 6 illustrates the multi-stage drug delivery system 100 in a state of delivering the second drug 110 to a user. That is, FIG. 6 can represent a state after the cannula 112 has pierced through the second plunger 106 and the second drug 110 is being delivered to the user but prior to all of the second drug 110 being extracted.

In various embodiments, the force 502 can generally be applied to drive the cannula 112 through the plungers 104 and 106. The force 502 can then be removed or stopped and the force 204 can be applied or reapplied to drive the first plunger 104 (and the second plunger 106 when appropriate) towards the end (e.g., a closed end) of the cartridge 102. That is, the force 502 may not be used to drive the plungers 104 and 106 to the end of the cartridge 102. The force 204 can be applied along any portion of the first plunger 104 (e.g., including one or more positions along any portion of the first plunger 104).

Figure 7:
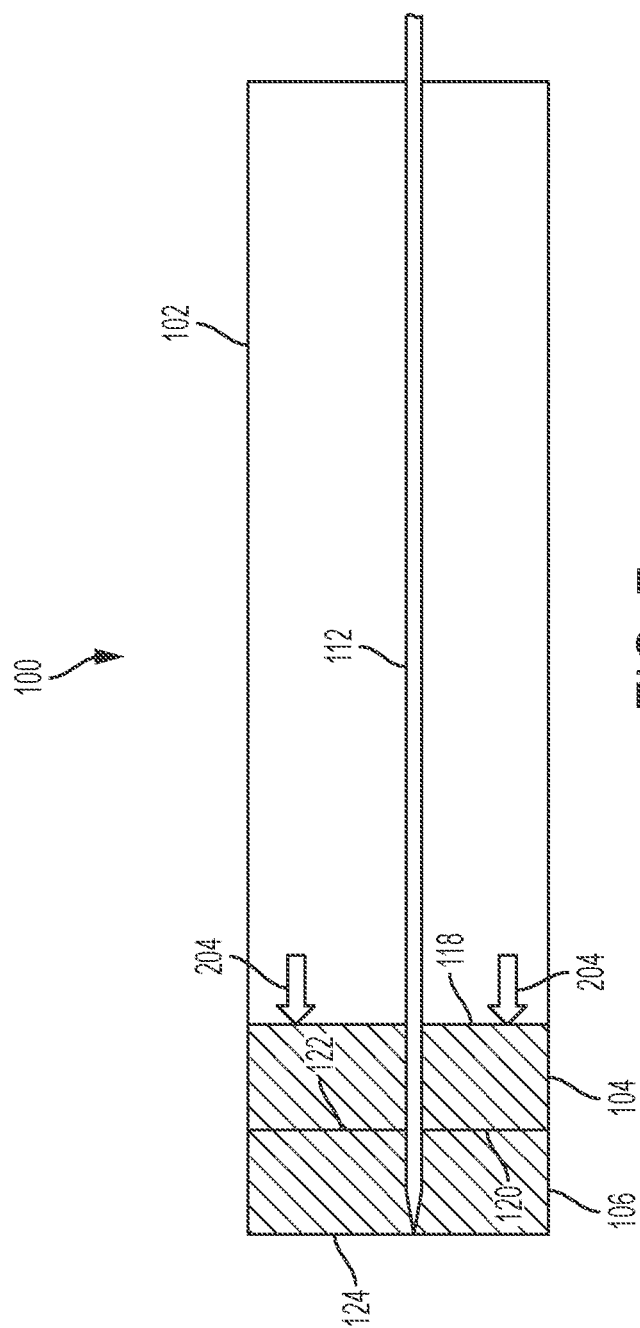
FIG. 7 illustrates the multi-stage drug delivery system of FIG. 1 in a sixth stage of operation.

FIG. 7 illustrates the multi-stage drug delivery system 100 after depletion of the second drug 110. That is, FIG. 7 shows the multi-stage drug delivery system 100 after all or approximately all of the second drug 110 has been extracted from the second chamber 116 of the multi-stage drug delivery system 100. As shown in FIG. 7, the first and second plungers 104 and 106 are positioned against the end of the cartridge 102 (e.g., adjacent to the end of the cartridge 102 such that no portion of the second drug 108 remains between the second plunger 106 and the end of the cartridge 102).

As shown in FIG. 7, the second plunger 106 has met the end of stroke. Accordingly, the delivery of the dosage of the second drug 110 is substantially complete (e.g., all of the second drug 110 has been forced out of the second chamber 116). FIG. 7 can represent a state of the multi-stage drug delivery system 100 after both the first and second drugs 108 and 110 have been delivered to the user. The multi-stage drug delivery system 100 can be re-used (e.g., re-filled) or can be discarded.

FIGS. 1-7 illustrate the multi-stage drug delivery system 100 having two chambers (e.g., chambers 114 and 116) but is not so limited. That is, the multi-stage drug delivery system 100 can include any number of chambers (and corresponding number of plungers) to store and subsequently dispense any number of different drugs, in any amount, according to any desired delivery schedule in accordance with the techniques described herein. FIGS. 1-7 can represent cross-sectional side views of the multi-stage drug delivery system 100 during various stages of operation as described herein.

Figure 8:
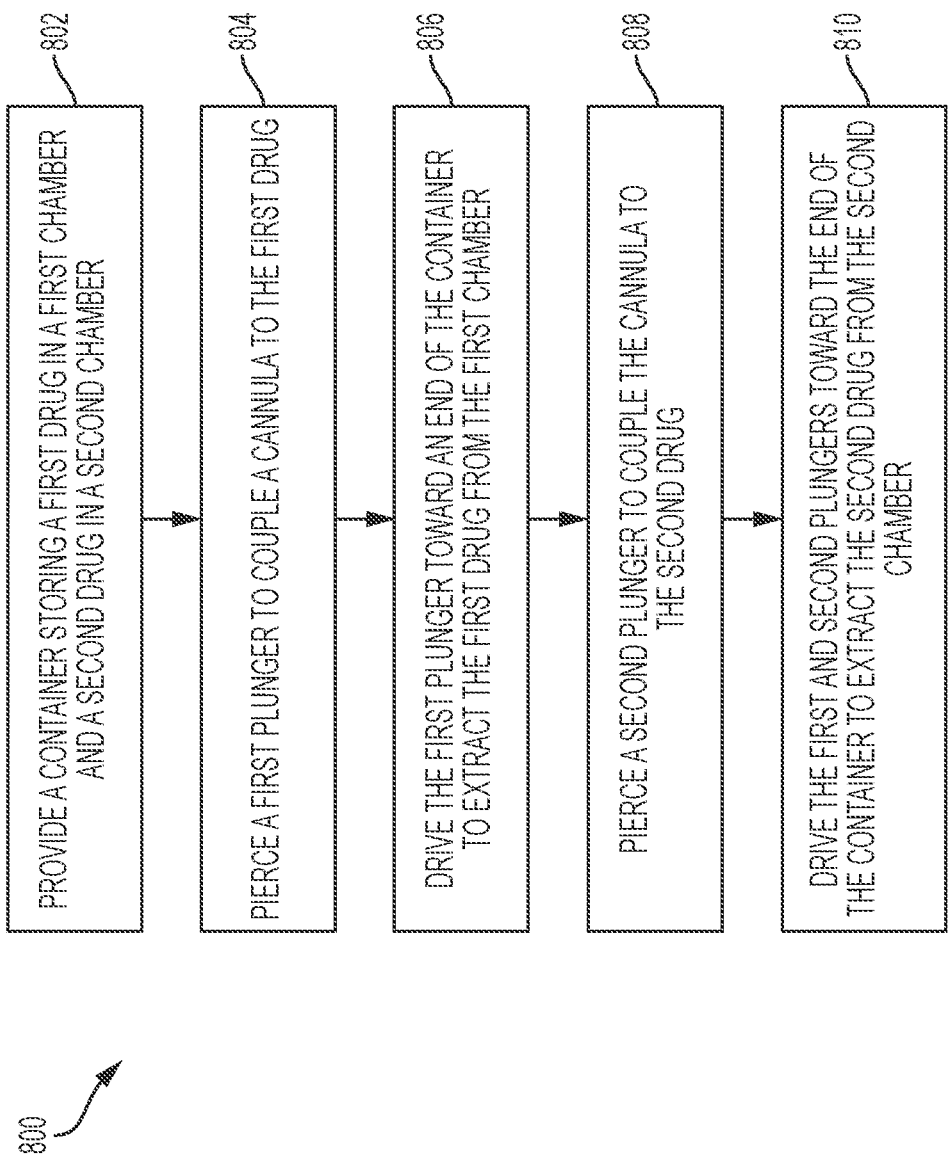
FIG. 8 illustrates an exemplary method for delivering multiple liquid drugs to a patient.

FIG. 8 illustrates a method 800 for delivering multiple liquid drugs to a patient using a multi-stage delivery system such as, for example, the multi-stage delivery system 100. The method 800 is described in relation to delivering two liquid drugs to the patient from the multi-stage delivery system but is not so limited. The method 800 is applicable to the delivery of any number of liquid drugs from a multi-stage delivery system configured to store a corresponding number of liquid drugs as will be appreciated by a person of ordinary skill in the art. Further, the method 800 is applicable to the delivery of different liquid drugs, to the delivery of different amounts of each liquid drug, and to the delivery of each liquid drug at different times and rates as will be appreciated by a person of ordinary skill in the art.

At 802, a container configured to store a first drug in a first chamber and configured to store a second drug in a second, different chamber can be provided. The first and second drugs can be liquid drugs. The first and second drugs can be any type of liquid drugs. The first and second liquid drugs can be the same or different drugs. The first and second chambers can be of the same size or can be configured to store different amounts of the first and second drugs, respectively.

The first and second drugs can be sealed and separated from each other. A first plunger positioned in the container, a second plunger positioned in the container and spaced apart from the first plunger, and the container can form the first chamber. The second plunger and the container can form the second chamber.

At 804, a cannula can pierce the first plunger. The cannula can be positioned at a center of the first plunger. The cannula can extend through the first plunger and into the first chamber. The cannula can extend into the first chamber by a desired amount or depth and can be coupled to the first drug.

The cannula can be coupled to the patient. Accordingly, when the cannula accesses the first drug stored in the first chamber the cannula can couple the first drug to the patient.

At 806, the first plunger is driven toward an end of the container. The first plunger is advanced further into the container toward the second plunger. The cannula can remain positioned in the first plunger as the first plunger is advanced. The second plunger can remain stationary. As a result of the first plunger moving further into the container, the first drug is expelled from the first chamber (e.g., as the size or volume of the first chamber is reduced). The expelled first drug can flow into and through the cannula and on to the patient.

The first plunger can be advanced to expel substantially all of the first drug. When substantially all of the first drug is expelled, the first plunger can be positioned against the second plunger.

At 808, the second plunger can be pierced by the cannula. The cannula can extend through the second plunger (and through the first plunger) and into the second chamber. The cannula can extend into the second chamber by a desired amount or depth and can be coupled to the second drug. Accordingly, when the cannula accesses the second drug stored in the second chamber the cannula can couple the second drug to the patient.

At 810, the first plunger and second plungers are driven toward the end of the container. The first and second plungers are advanced further into the container toward a closed end of the container. The cannula can remain positioned in the first and second plungers as the first and second plungers are advanced. As a result of the first and second plungers moving further into the container, the second drug is expelled from the second chamber (e.g., as the size or volume of the second chamber is reduced). The expelled second drug can flow into and through the cannula and on to the patient.

The first and second plungers can be advanced to expel substantially all of the second drug. When substantially all of the second drug is expelled, the second plunger can be positioned against the closed end of the container with the first plunger positioned against the second plunger.

The following examples pertain to additional further embodiments:

Example 1 is a multiple stage drug delivery system, comprising a cartridge, a first plunger positioned in the cartridge, and a second plunger positioned in the cartridge, wherein the first plunger, the second plunger, and the cartridge form a first chamber configured to store a first liquid drug, and the second plunger and the cartridge form a second chamber configured to store a second liquid drug.

Example 2 is an extension of Example 1 or any other example disclosed herein, further comprising a cannula configured to pierce the first plunger to access the first liquid drug stored in the first chamber.

Example 3 is an extension of Example 2 or any other example disclosed herein, further comprising a cannula insertion component coupled to the cannula.

Example 4 is an extension of Example 3 or any other example disclosed herein, wherein the cannula insertion component comprises one or more springs.

Example 5 is an extension of Example 3 or any other example disclosed herein, wherein the cannula is coupled to a patient, wherein the cannula couples the first liquid drug stored in the first chamber to the patient when the cannula accesses the first chamber.

Example 6 is an extension of Example 5 or any other example disclosed herein, further comprising a drive component configured to advance the first plunger toward the second plunger, thereby extracting the first liquid drug from the first chamber for delivery to the patient through the cannula.

Example 7 is an extension of Example 6 or any other example disclosed herein, wherein the drive component comprises one or more springs.

Example 8 is an extension of Example 6 or any other example disclosed herein, wherein the drive component comprises an electromechanical system.

Example 9 is an extension of Example 6 or any other example disclosed herein, wherein the cannula is configured to pierce the second plunger to access the second liquid drug stored in the second chamber after the first liquid drug is extracted from the first chamber.

Example 10 is an extension of Example 9 or any other example disclosed herein, wherein the cannula couples the second liquid drug stored in the second chamber to the patient when the cannula accesses the second chamber.

Example 11 is an extension of Example 9 or any other example disclosed herein, wherein the first plunger is positioned adjacent to the second plunger after the first drug is extracted from the first chamber.

Example 12 is an extension of Example 11 or any other example disclosed herein, wherein the drive component is configured to advance the first plunger and the second plunger toward an end of the cartridge, thereby extracting the second liquid drug from the second chamber for delivery to the user through the cannula.

Example 13 is an extension of Example 12 or any other example disclosed herein, wherein the first drug is dispensed over a first amount of time at a first rate and the second drug is dispensed over a second amount of time at a second rate.

Example 14 is an extension of Example 13 or any other example disclosed herein, wherein the first amount of time and the second amount of time are non-overlapping.

Example 15 is an extension of Example 13 or any other example disclosed herein, wherein the first and second rates are different.

Example 16 is an extension of Example 1 or any other example disclosed herein, wherein the first and second plungers are elastomeric plungers.

Example 17 is an extension of Example 1 or any other example disclosed herein, wherein the first and second liquid drugs are different drugs.

Example 18 is an extension of Example 1 or any other example disclosed herein, wherein the first chamber and the second chamber have different volumes.

Example 19 is an extension of Example 1 or any other example disclosed herein, wherein the cartridge comprises glass.

Example 20 is a method, comprising providing a container configured to store a first liquid drug in a first chamber and a second liquid drug in a second chamber, piercing a first plunger with a cannula to couple the cannula to the first liquid drug, driving the first plunger toward an end of the container to extract the first liquid drug from the first chamber through the cannula, piercing a second plunger with the cannula to couple the cannula to the second liquid drug, and driving the first and second plungers toward the end of the container to extract the second liquid drug from the second chamber through the cannula.

Example 21 is an extension of Example 21 or any other example disclosed herein, further comprising piercing the second plunger after substantially all of the first liquid drug is extracted from the first chamber.

Example 22 is an extension of Example 21 or any other example disclosed herein, further comprising piercing the second plunger after a predetermined delay.

Example 23 is an extension of Example 22 or any other example disclosed herein, further comprising extracting the first liquid drug from the first chamber at a first rate and extracting the second liquid drug from the second chamber at a second, different rate.

Example 24 is an extension of Example 23 or any other example disclosed herein, wherein the first and second liquid drugs are different liquid drugs.

Example 25 is an extension of Example 20 or any other example disclosed herein, further comprising sealing the first chamber with the container and the first and second plungers and sealing the second chamber with the container and the second plunger.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

The invention claimed is:

1. A multiple stage drug delivery system, comprising:
   a cartridge;
   a first plunger positioned in the cartridge;
   a second plunger positioned in the cartridge, wherein:
      the first plunger, the second plunger, and the cartridge form a first chamber configured to store a first liquid drug, and
      the second plunger and the cartridge form a second chamber configured to store a second liquid drug;
   a cannula configured to pierce through the first plunger and the second plunger; and
   a cannula insertion component coupled to the cannula and including one or more springs, the cannula insertion component configured to, in response to being triggered, cause the cannula to pierce the first plunger, wherein:
      the first plunger is configured to:
         move toward the second plunger, and
         expel the first liquid drug from the first chamber through the cannula in a direction opposite movement of the first plunger toward the second plunger.

2. The multiple stage drug delivery system of claim 1, wherein the cannula is further configured to access the first liquid drug stored in the first chamber after piercing the first plunger.

3. The multiple stage drug delivery system of claim 1, wherein the cannula is coupled to a fluid path that is configured to deliver the first liquid drug stored in the first chamber to a patient when the cannula accesses the first chamber.

4. The multiple stage drug delivery system of claim 1, wherein the first plunger and the second plunger are elastomeric plungers.

5. The multiple stage drug delivery system of claim 1, wherein the first and second liquid drugs are different drugs.

6. The multiple stage drug delivery system of claim 1, wherein the first chamber and the second chamber have different volumes.

7. The multiple stage drug delivery system of claim 1, wherein the cartridge comprises glass.

8. The multiple stage drug delivery system of claim 1, further comprising:
   a drive component, wherein the drive component:
      includes one or more springs, different from the one or more springs of the cannula insertion component, and
      is configured to apply a force to the first plunger that advances the first plunger toward the second plunger, thereby extracting the first liquid drug from the first chamber for delivery to the patient through the cannula.

9. The multiple stage drug delivery system of claim 8, wherein the cannula is configured to pierce the second plunger to access the second liquid drug stored in the second chamber after the first liquid drug is extracted from the first chamber.

10. The multiple stage drug delivery system of claim 9, wherein the cannula couples the second liquid drug stored in the second chamber to the fluid path configured to deliver the second liquid drug to the patient when the cannula accesses the second chamber.

11. The multiple stage drug delivery system of claim 9, wherein the first plunger is positioned adjacent to the second plunger after the first drug is extracted from the first chamber.

12. The multiple stage drug delivery system of claim 8, wherein the drive component is configured to advance the first plunger and the second plunger toward an end of the cartridge, thereby extracting the second liquid drug from the second chamber for delivery to the user through the cannula.

13. The multiple stage drug delivery system of claim 12, wherein the first drug is dispensed over a first amount of time at a first rate and the second drug is dispensed over a second amount of time at a second rate.

14. The multiple stage drug delivery system of claim 13, wherein the first amount of time and the second amount of time are non-overlapping.

15. The multiple stage drug delivery system of claim 13, wherein the first and second rates are different.

16. The multiple stage drug delivery system of claim 8, wherein the drive component is further configured to:
   apply a force to the first plunger that advances the first plunger toward the second plunger.

17. A method, comprising:
   providing a container configured to store a first liquid drug in a first chamber and a second liquid drug in a second chamber;
   actuating a cannula insertion component to apply a force to a cannula to pierce the cannula through a first plunger to couple the cannula to the first liquid drug;
   driving the first plunger, by applying another force to the first plunger by a drive component coupled to the first plunger, toward an end of the container to extract the first liquid drug from the first chamber through the cannula in a direction opposite to a direction in which the first plunger is being driven;
   piercing through a second plunger with the cannula to couple the cannula to the second liquid drug; and
   driving the first and second plungers together toward the end of the container to extract the second liquid drug from the second chamber through the cannula.

18. The method of claim 17, further comprising piercing the second plunger after substantially all of the first liquid drug is extracted from the first chamber.

19. The method of claim 17, further comprising piercing the second plunger after a predetermined delay.

20. The method of claim 17, further comprising extracting the first liquid drug from the first chamber at a first rate and extracting the second liquid drug from the second chamber at a second, different rate.

21. The method of claim 17, wherein the first liquid drug and second liquid drug are different liquid drugs.

22. The method of claim 17, further comprising sealing the first chamber with the container and the first and second plungers and sealing the second chamber with the container and the second plunger.

\* \* \* \* \*